United States Patent [19]

Lin et al.

[11] 4,414,410

[45] Nov. 8, 1983

[54] PROCESS FOR PREPARING ALKYL ESTERS BY HOMOLOGATION OF THE NEXT LOWER ALKYL ESTER

[75] Inventors: Jiang-Jen Lin, Round Rock; John F. Knifton, Austin, both of Tex.

[73] Assignee: Texaco Inc., White Plains, N.Y.

[21] Appl. No.: 339,232

[22] Filed: Jan. 13, 1982

[51] Int. Cl.$^3$ .................. C07C 67/36; C07C 69/003; C07C 69/14

[52] U.S. Cl. .................. 560/265; 260/404; 260/404.5; 260/408; 260/410.9 R; 260/465.4; 260/409; 546/319; 546/327; 549/484; 560/1; 560/19; 560/100; 560/103; 560/105; 560/122; 560/123; 560/124; 560/127; 560/155; 560/169; 560/178; 560/186; 560/187; 560/190; 560/204; 560/226; 560/227; 560/121; 562/517

[58] Field of Search .............. 560/265, 204, 103, 105, 560/114, 100, 127, 178, 187, 226, 175, 227, 121, 64, 155, 1, 19, 122–124, 232, 190; 260/408, 404, 404.5, 410.9 R, 409; 568/902; 546/319, 327; 549/484

[56] References Cited

U.S. PATENT DOCUMENTS

| 4,189,441 | 2/1980 | Braca et al. | 560/232 |
| 4,239,924 | 12/1980 | Pretzer et al. | 560/265 |

*Primary Examiner*—Vivian Garner
*Attorney, Agent, or Firm*—Jack H. Park; Carl G. Ries; Walter D. Hunter

[57] ABSTRACT

Alkyl esters, such as ethyl acetate, are prepared by contacting the corresponding next lower carbon number alkyl ester, such as methyl acetate, with carbon monoxide and hydrogen in the presence of an iodine or iodide-free catalyst composition comprising a ruthenium-containing compound, a cobalt containing compound and a quaternary phosphonium salt or base, and heating the mixture to an elevated temperature and pressure for sufficient time to produce the desired higher alkyl ester, and then recovering the same from the reaction mixture.

24 Claims, No Drawings

PROCESS FOR PREPARING ALKYL ESTERS BY HOMOLOGATION OF THE NEXT LOWER ALKYL ESTER

BACKGROUND OF THE INVENTION

1. Field of the Invention

This invention relates to a new process for preparing alkyl esters. More particularly, the invention relates to an improved process for preparing alkyl esters by the homologation of the corresponding next lower alkyl ester.

Specifically, the invention provides a new and improved process for preparing alkyl carboxylic acid esters, and preferably the ethyl esters of aliphatic carboxylic acids such as ethyl acetate, by the homologation of the corresponding next lower carbon number alkyl ester, such as the methyl ester, which process comprises contacting the lower carbon number alkyl ester with carbon monoxide and hydrogen in the presence of an iodide-or iodine-free catalyst composition comprising a ruthenium-containing compound, a cobalt-containing compound and a quaternary phosphonium salt or base and heating the resulting mixture to an elevated temperature and pressure for sufficient time to produce the desired higher carbon number alkyl ester, and removing the same from the reaction mixture.

2. Prior Art

Ethyl esters, such as ethyl acetate, are chemicals which have found wide use in industry. In addition to their use as solvents and diluents they may be pyrolyzed to form the valuable ethylene monomer.

Various methods have been used in the past for the production of the ethyl esters. The esters can be produced, for example, by reaction of the ethanol with the desired carboxylic acid, both components commonly being obtained from petroleum or agrichemical feedstocks. Synthesis of the ethyl esters from syngas would potentially be more economical and desirable.

It has been proposed, for example, to prepare methyl acetate from syngas and then convert the methyl acetate to the ethyl ester by further treatment with the syngas. British patent application No. 2,001,070A for instance, discloses a method for converting methyl acetate to ethyl acetate by use of a carbonylation catalyst containing cobalt and iodine. This method is limited, however, as it utilizes iodide-or iodine-containing promoters which are corrosive and difficult to utilize on a large commercial scale.

It is an object of the invention, therefore, to provide a new and improved process for preparing higher carbon number alkyl esters. It is a further object to provide a process for preparing alkyl esters from lower carbon number alkyl esters using a new and improved catalyst system. It is a further object to provide a new process for preparing ethyl esters from methyl esters of aliphatic carboxylic acids which gives good selectivity and yield of desired product. It is a further object to provide a process for preparing ethyl esters from methyl esters which avoids the use of iodine and iodide components and is adaptable for use on a large commercial scale. These and other objects will be apparent from the following detailed description thereof.

SUMMARY OF THE INVENTION

It has now been discovered that these and other objects may be accomplished by the process of the invention comprising contacting the lower carbon number alkyl ester, such as the methyl ester, with carbon monoxide and hydrogen in the presence of an iodide- or iodine-free catalyst composition comprising a ruthenium-containing compound, such as for example, ruthenium oxide, a cobalt-containing compound, such as dicobalt octacarbonyl, and a quaternary phosphonium salt or base, such as heptyltriphenylphosphonium bromide, and heating the resulting mixture at an elevated temperature and pressure for sufficient time to produce the higher carbon number alkyl ester, such as the ethyl ester, and then recovering the same from the reaction mixture. It was surprising to find that this new catalyst system was highly selective for the conversion of the methyl esters to the ethyl esters in view of the discouraging results obtained with related catalyst systems. A further advantage of the process being that it avoids the use of iodide or iodine or other promoters which are corrosive and difficult to utilize in large scale commercial operations.

The process of the invention is particularly characterized by the good selectivity in the conversion of the methyl esters to the corresponding ethyl esters as represented by the following equation:

$$RCOOCH_3 + CO + 2H_2 \rightarrow RCOOC_2H_5 + H_2O \qquad (1)$$

Typical conversion of the lower alkyl esters to the higher alkyl esters generally range from about 63% to about 100% with selectivities to ethyl ester of up to 73%. Valuable by-products of the reaction include even higher esters, such as the propyl and butyl esters, as well as minor amounts of other oxygenated by-products, such as acetic acid.

DETAILED DESCRIPTION OF THE INVENTION

In the operation of the process of the invention, the higher alkyl ester, along with the above-noted by-products, are produced concurrently from the lower alkyl ester, carbon monoxide and hydrogen by a process comprising the following steps:

(a) contacting a mixture of the lower carbon number alkyl ester, carbon monoxide and hydrogen with an iodide- or iodine-free catalyst comprising a ruthenium-containing compound, a cobalt-containing compound, and a quaternary phosphonium salt or base, said reaction mixture can and sometimes preferably does contain a solvent, such as p-dioxane, (b) heating the said mixture to an elevated temperature, e.g. about 150° C., and an elevated pressure, e.g. about 500 psi, with sufficient carbon monoxide and hydrogen to satisfy the stoichiometry of the desired higher carbon number alkyl ester synthesis as noted above, until substantial formation of the desired ester has been achieved, and, (c) preferably isolating the said higher alkyl ester and minor by-products from the reaction mixture, as by distillation.

In order to present the inventive concept of the present invention in the greatest possible detail, the following supplementary disclosure is submitted. The process of the invention is practiced as follows:

As noted, the new catalyst system used in the process of the invention contains a ruthenium-containing compound, a cobalt-containing compound and a phosphonium salt or base. The ruthenium-containing compound employed as catalyst may take many different forms.

For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, tricarbonyl ruthenium nitrate, or as the salt of a suitable organic carboxylic acid, for example, ruthenium(III) acetate, ruthenium propionate, ruthenium naphthenate, ruthenium valerate and ruthenium complexes with carbonyl-containing ligands such as ruthenium(III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $(Ru(CO)_3Cl_2)_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The cobalt-containing compound to be used in the catalyst composition may take many different forms. For instance, the cobalt may be added to the reaction mixture in the form of an oxide, salt, carbonyl derivative and the like. Examples of these include, among others, cobalt oxides $Co_2O_3$, $Co_3O_4$, CoO, cobalt(II) bromide, cobalt chloride, cobalt(II) thiocyanate, cobalt(II) hydroxide, cobalt(II) carbonate, cobalt(II) nitrate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_3$, tetracobalt dodecacarbonyl $Co_4(CO)_{12}$ and hexacobalt hexadecacarbonyl $Co_8(CO)_{16}$ and derivatives thereof by reaction with ligands, and preferably group V donors, such as the phosphines, arsines and stibine derivatives such as $(Co(CO)_3L)_2$ wherein L is $PR_3$, $AsR_3$ and $SbR_3$ wherein R is a hydrocarbon radical, cobalt carbonyl hydrides, cobalt carbonyl bromides, cycloalkadienyl cobalt carbonyls, cobalt nitrosyl carbonyls as $CoNO(CO)_3$, $Co(NO)CO)_2PPh_3$, cobalt nitrosyl bromide, organometallic compounds obtained by reacting cobalt carbonyls with olefins, allyl and acetylene compounds, such as bis($\eta$-cyclopentadienyl) cobalt ($\pi C_5H_5)_2Co$, cyclopentadienyl cobalt dicarbonyl, bis(hexamethylenebenzene)cobalt.

Preferred cobalt-containing compounds to be used in the catalyst system comprise those having at least one cobalt atom attached to carbon, such as the cobalt carbonyls and their derivatives as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl bromides, cobalt carbonyl hydrides, cobalt nitrosyl carbonyls, and the like, and mixtures thereof.

Particularly preferred cobalt-containing compounds to be used in the catalyst comprise those having at least one cobalt atom attached to at least three separate carbon atoms, such as for example, the dicobalt octacarbonyls and their derivatives.

The quaternary onium salt or base to be used in the catalyst composition may be any phosphonium salt or base, but are preferably the quaternary phosphonium salts having the formula

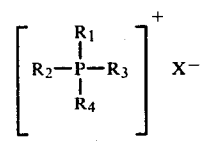

wherein $R_1$, $R_2$, $R_3$ and $R_4$ are organic radicals, particularly alkyl, aryl or alkaryl radicals bonded to the phosphorus atom, and X is an anionic species. The organic radicals useful in this instance include those alkyl radicals having 1 to 20 carbon atoms in a branched or linear alkyl chain, such as methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxide, nitrates, chromates, tetrafluoroborates and the corresponding chlorides, are also satisfactory in this instance.

Equally useful are the phosphonium salts containing phosphorus bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to the phosphorus atom through the aryl function. The quaternary phosphonium salt can be a tetrahydrocarbylphosphonium salt having from 1-10 carbon atoms in each of the hydrocarbyl groups.

Illustrative examples of suitable quaternary phosphonium bases and salts include tetrabutylphosphonium bromide, heptyltriphenylphosphonium bromide, tetrabutylphosphonium hydroxide, tetrabutylphosphonium chromate, tetrabutylphosphonium tetrafluoroborate, tetrahexylphosphonium acetate, tetraoctylphosphonium bromide.

The preferred quaternary salts are generally the tetralkylphosphonium salts containing alkyl groups having 1 to 6 carbon atoms, such as methyl, ethyl, butyl, amyl, hexyl and isobutyl. Tetrabutylphosphonium salts, such as the tetrabutylphosphonium bromides and chlorides, acetate and chromate salts and hydroxide base, are the most preferred.

The quantity of the ruthenium-containing compound and the cobalt-containing compound to be used in the process of the invention may vary over a wide range. The process is conducted in the presence of a catalytically effective quantity of the active ruthenium-containing compound and the active cobalt-containing compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the cobalt-containing compound, or even lesser amounts, based on the total weight of the reaction mixture. The upper concentration is dictated by a variety of factors including catalyst cost, partial pressures of carbon monoxide, operating temperature, etc. A ruthenium-containing compound concentration of from about $1 \times 10^{-5}$ to about 10 weight percent in conjunction with a cobalt-containing compound concentration of from about $1 \times 10^{-5}$ to about 5 percent, based on the total weight of the reaction mixture is generally desirable in the practice of this invention. The preferred ruthenium to cobalt atomic ratios are from about 10:1 to 1:10.

Generally, in the catalyst system used in the process of the invention, the molar ratio of the ruthenium-containing compound to the quaternary onium salt or base will range from about 1:0.01 to about 1:100 or more, and preferably will be form about 1:1 to about 1:20.

Particularly superior results are obtained when the above-noted three components of the catalyst system are combined in a molar basis as follows: ruthenium-containing compound 0.1 to 4 moles, cobalt-containing compound 0.025 to 1.0 moles and the quaternary onium salt or base 0.4 to 60 moles, and still more preferably when the components are combined in the following molar ratios; ruthenium-containing compound 1 to 4 moles, cobalt-containing compound 0.25 to 1.0 moles and the quaternary onium base or salt 10 to 50 moles.

The lower carbon number alkyl esters used in the process of the invention may be any suitable lower alkyl ester of a carboxylic acid. The alkyl ester portion may be derived from any of the lower alkanols, such as methanol, ethanol, propanol, butanol and the like, and substituted derivatives. Preferably the alcohol portion is derived from lower alkanols containing from 1 to 4 carbon atoms. The carboxylic acid portion may be derived from any suitable carboxylic acid including the aliphatic acids, alicyclic monocarboxylic acids, heterocyclic acids and aromatic acids, substituted or unsubstituted. Examples of such acids include, among others, the lower monoaliphatic carboxylic acids, such as formic acid, acetic acid, propionic acid, butyric acid, isobutyric acid, valeric, caproic, capric, perlargonic and lauric acids, together with dicarboxylic acids, such as oxalic, malonic, succinic and adipic acids. The invention further contemplates the use of substituted monocarboxylic acids containing one or more functional substituents such as the lower alkoxy, chloro, fluoro, cyano, amino functional groups, examples of which include acetoacetic acid, dichloroacetic acid and trifluoroacetic acid, chloropropionic acid, trichloroacetic acid, and the like. Among the suitable aromatic acids contempleted are benzoic acid, naphthoic acid, toluic acid, chlorobenzoic acids, aminobenzoic acids, and phenylacetic acid. The alicyclic monocarboxylic acids may contain from 3 to 6 carbon atoms in the ring, both substituted or unsubstituted, and may contain one or more carboxyl groups, such as cyclopentanecarboxylic acid and hexahydrobenzoic acids. The heterocyclic acids may contain 1 to 3 fused rings both substituted and unsubstituted together with one or more carboxylic groups, examples include quinolinic, furoic and picolinic acids. Mixtures of said classes of carboxylic acids, in any ratio, may also be used.

Preferred carboxylic acids include the lower monocarboxylic acids containing from 1 to 12 carbon atoms, and the dicarboxylic acids containing up to 12 carbon atoms.

Examples of the esters of the above acids that can be used in the process of the invention include, among others, methyl acetate, methyl propionate, methyl butyrate, ethyl benzoate, methyl perlargonate, ethyl valerate, dimethyl malonate, methyl chloracetate, methyl laurate, propyl isobutyrate, diethyl succinate, methyl toluate, and the like, and mixtures thereof.

The amount of the lower carbon number alkyl ester to be used in the process of the invention may vary over a wide range. In general, the amount of the ester to be used should be sufficient to satisfy the stoichiometry of the formation of the esters as shown above, although larger or smaller amounts may be used as desired or necessary.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not undergo reaction under carbon monoxide hydrogenation conditions, such as carbon dioxide, hydrocarbons, such as methane, ethane, propane and the like, ethers such as dimethyl ether, methyl ethyl ester and diethyl ether, and higher alcohols.

Solvents may be and sometimes preferably are employed in the process of the invention. Suitable solvents for the process include the oxygenated hydrocarbons, e.g. compounds possessing only carbon, hydrogen and oxygen and one in which the oxygen atom present is in an ether, ester, ketone carbonyl or hydroxyl group or groups. Generally, the oxygenated hydrocarbon will contain from about 3 to 12 carbon atoms and preferably a maximum of three oxygen atoms. The solvent must be substantially inert under the reaction conditions, must be relatively non-polar and must be one which has a normal boiling point of at least 65° C. at atmospheric pressure and preferably the solvent will have a boiling point greater than that of the ester and other products of the reaction so that recovery of the solvent by distillation is facilitated.

Preferred ester type solvents are the aliphatic, cycloaliphatic and aromatic carboxylic acid esters as exemplified by methyl benzoate, isopropyl benzoate, butyl cyclohexanoate, as well as dimethyl adipate. Useful alcohol-type solvents include the monohydric alcohols as cyclohexanol and 2-octanol, etc. Suitable ketone-type solvents include, for example, cyclic ketones, such as 2-pentanone, butanone, acetophenone, etc. Ethers which may be utilized as solvents include cyclic, acyclic, and heterocyclic materials. Preferred ethers are the heterocyclic ethers as illustrated by p-dioxane and 1,3-dioxane. Other suitable ethers include isopropyl dibutyl ether, diethylene glycol dibutyl ether, diphenyl ether, dibutyl ether, heptyl phenyl ether, anisole, tetrahydrofurane, etc. The most useful solvents of all of the above groups include the ethers, as represented by the polycyclic, heterocyclic ethers such as diphenyl ether and 1,4-dioxane, etc.

The amount of the solvent employed may vary over a wide range. In general, it is desirable to use sufficient solvent to fluidize the catalyst system.

The temperature range which can usefully be employed in the process of the invention may vary over a considerable range depending upon experimental facts, including the choice of catalyst, pressure and other variables. The preferred temperatures are above 150° C. and more preferably between 160° C. and 350° C. when superatmospheric pressures of syngas are employed.

Coming under special consideration are the temperatures ranging from about 180° C. to about 250° C.

Superatmospheric pressures of about 500 psi or greater lead to substantial yield of the desired esters. A preferred range is from about 1000 psi to about 7500 psi, although pressures above 7500 also provide useful yields of the desired products. The pressures referred to herein represent the total pressure generated by all the reactants, although they are substantially due to the carbon monoxide and hydrogen reactants.

The desired products of the reaction, the ethyl esters of the desired alkanoic acids, will be formed at product selectivities varying from about 23 wt% to about 73 wt%. Also formed will be minor by-products, such as the propyl and butyl esters of those alkanoic acids as well as other oxygenated products such as acetic acid. The desired products can be recovered from the reaction mixture by conventional means, such as fractional distillation in vacuo, etc.

The process of the invention can be conducted in a batch, semi-continuous or continuous manner. The catalyst can be initially introduced into such a zone during the course of the synthesis reaction. Operating conditions can be adjusted to optimize the formation of the desired esters, and said material can be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures; viz, gas-liquid phase chromatography (glc), infrared (ir) mass spectrometry, nuclear magnetic resonance (nmr) and elemental analyses, or a combination of these techniques. Analyses have, for the most part, been by weight; all temperatures are in degree centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the unexpected results obtained by using the new catalyst composition in the homologation of methyl ester to ethyl ester.

A glass liner was charged with 1 mmole (0.19 g) of ruthenium dioxide hydrate, 0.25 mmole (0.085 g) of dicobalt octacarbonyl and 10 mmole (4.25 g) of n-heptyltriphenylphosphonium bromide and 0.15 moles (11.0 g) of methyl acetate. The glass liner was placed in a stainless steel reactor and purged of air with hydrogen and carbon monoxide (1:1 molar ratio), and then pressured to 2000 psi and heated to 220° C. The pressure was raised to about 6300 psi. After 18 hours, the pressure dropped to 3975 psi. The reactor was allowed to cool, the gas pressure noted (2400 psi), and the excess gas vented and the liquid product recovered (19.7 g).

The liquid product was subjected to analysis by glc, and a typical fraction was shown to comprise:
73 wt% ethyl acetate
22 wt% acetic acid
1.5 wt% water
less than 1.0 wt% unreacted methyl acetate Estimated yield of ethyl acetate, based on methyl acetate charged, is 81 mol%. Selectivity to ethyl acetate, based upon product distribution, is 73%.

EXAMPLES II TO VIII

Following the procedure of Example I, homologation of methyl acetate (9.3 to 11.0 g) to ethyl acetate was effected using a catalyst comprising 1.0 mmole ruthenium oxide hydrate, 10.0 mmole n-heptyltriphenylphosphonium bromide and 0.25 mmole dicobalt octacarbonyl. Over the operative temperature range of 180°-220° C., operative pressures of 4500 to 7300 psi and reaction periods of 5 to 18 hours, the conversion of methyl acetate and selectivities to ethyl acetate, propyl acetate and n-butyl acetate are summarized in Table I.

TABLE I

| | | | | Product Selectivities, wt. % | | | | |
|---|---|---|---|---|---|---|---|---|
| example | Reaction conditions[a] | methyl acetate (g) charged | methyl acetate conversions (wt %) | ethyl acetate | acetic acid | n-propyl acetate | n-butyl acetate | weight gain (g) |
| II | 4500 psi (constant) 180° C. 18 hrs. | 11.0 | 63 | 59 | 38 | 3 | 0 | 2.0 |
| III | 5000 psi (constant) 220° C., 18 hrs. | 11.0 | 97 | 37 | 47 | 12 | 0 | 5.5 |
| IV | 7300 → 5770 psi 220° C., 4 hrs. | 11.0 | 82 | 59 | 38 | 3 | 0 | 4.0 |
| V | 6300 psi (constant) 220° C., 18 hrs. | 11.0[c] | 100 | 40 | 33 | 18 | 0 | 5.0 |
| VI | 6450 → 5700 psi 220° C., 66 hrs. | 11.0 | 100 | 23 | 25 | 28 | 10 | 6.5 |
| VII | 6750 → 5000 psi[b] 220° C., 18 hrs. | 11.0 | 99 | 52 | 21 | 15 | 1 | 2.0 |
| VIII | 5500 psi (constant)[b] 200° C., 5 hrs. | 9.3 | 66 | 58 | 24 | 3 | 0 | 1.5 |

[a]CO/H$_2$ = 1:1
[b]CO/H$_2$ = 1:2
[c]1 in 12.0 grams of p-dioxane

EXAMPLE IX

Example I is repeated with the exception that the ruthenium dioxide hydrate is replaced with equivalent amounts of triruthenium dodecacarbonyl. Related results are obtained.

EXAMPLE X

Example I is repeated with the exception that the methyl acetate is replaced with methyl propionate. Related results are obtained.

What is claimed is:

1. A process for preparing a higher carbon number alkyl ester of an unsubstituted aliphatic carboxylic acid or an aromatic carboxylic acid selected from benzoic acid, naphthoic acid, toluic acid and phenylacetic acid, or an unsubstituted alicyclic monocarboxylic acid by homologation of the corresponding next lower carbon number alkyl ester which comprises contacting the lower alkyl ester with carbon monoxide and hydrogen in the presence of catalytic amounts of an iodide- or iodine-free catalyst composition comprising a ruthenium-containing compound, a cobalt-containing compound and a quaternary phosphonium salt or base, and heating the resulting mixture to a temperature above 150° C. and increasing the pressure to above 500 psi for a sufficient time to produce the desired alkyl ester.

2. A process as in claim 1 wherein the lower carbon number alkyl ester is an alkyl ester of a monocarboxylic acid containing from 1 to 12 carbon atoms.

3. A process as in claim 1 wherein the lower carbon number alkyl ester is a methyl ester of an aliphatic monocarboxylic acid containing up to 6 carbon atoms.

4. A process as in claim 1 wherein the lower carbon number alkyl ester is a methyl alkanoate.

5. A process as in claim 1 wherein the lower carbon number alkyl ester is methyl acetate.

6. A process as in claim 1 wherein the ruthenium-containing compound is a member of the group consisting of one or more oxides of ruthenium, ruthenium(III) acetylacetonate, ruthenium salts of carboxylic acids and ruthenium-carbonyl and hydrocarbonyl compounds.

7. A process as in claim 1 wherein the ruthenium-containing compound is a member of the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate, and triruthenium dodecacarbonyl.

8. A process as in claim 1 wherein the cobalt-containing compound is a cobalt carbonyl.

9. A process as in claim 1 wherein the cobalt-containing compound is a cobalt chloride or bromide.

10. A process as in claim 1 wherein the cobalt-containing compound is dicobalt octacarbonyl.

11. A process as in claim 1 wherein the ruthenium-containing compound is a ruthenium oxide hydrate.

12. A process as in claim 1 wherein the ruthenium-containing compound is a ruthenium chloride or bromide.

13. A process as in claim 1 wherein the quaternary phosphonium salt or base is a tetrahydrocarbylphosphonium salt.

14. A process as in claim 1 wherein the quaternary phosphonium salt or base is a tetrahydrocarbylphosphonium salt having from 1 to 10 carbon atoms in each of the hydrocarbyl groups.

15. A process as in claim 14 wherein the salt is selected from the group consisting of tetrahydrocarbylphosphonium bromides, chlorides and chromates.

16. The process of claim 1 wherein the process is undertaken in the presence of an inert solvent.

17. The process of claim 16 wherein the inert solvent is selected from the group consisting of p-dioxane, diphenyl ether and 2-pentanone.

18. A process as in claim 1 wherein the catalyst components are utilized in the following molar ratios: ruthenium-containing compound 0.1 to 4 moles: cobalt-containing compound 0.025 to 1.0 mole: quaternary phosphonium salt or base 0.4 to 60 moles.

19. A process as in claim 1 wherein the reaction is conducted at a temperature between 160° C. and 350° C.

20. A process as in claim 1 wherein the reaction is conducted at a pressure between 1000 psi and 7500 psi.

21. A process as in claim 20 wherein the ruthenium compound is a ruthenium oxide, the cobalt compound is a cobalt carbonyl and the phosphonium salt is a tetrahydrocarbylphosphonium bromide.

22. A process as in claim 1 wherein the quaternary phosphonium salt or base is n-heptyltriphenylphosphonium bromide.

23. A process for preparing ethyl esters of alkanoic acids from the methyl ester of the alkanoic acid which comprises contacting the methyl ester with carbon monoxide and hydrogen in the presence of a catalytic amount of an iodide- or iodine-free catalyst comprising a ruthenium-containing compound, a cobalt-containing compound and a quaternary phosphonium salt, and heating the resulting mixture to a temperature about 150° C. and a pressure of at least 1000 psi for sufficient time to produce the desired ethyl ester and then recovering the same from the reaction mixture.

24. A process as in claim 1 wherein the cobalt-containing compound is a member of the group consisting of cobalt carbonyls containing a group V donor ligand from the group consisting of phosphines, arsines and stibine derivatives of the formula $(Co(CO)_3L)_2$ wherein L is $PR_3$, $AsR_3$ and $SbR_3$ wherein R is a hydrocarbon radical, cobalt carbonyl hydrides, cobalt nitrosyl carbonyls, cycloalkadienyl cobalt carbonyls, cobalt bromides, cobalt oxides and cobalt salts of organic carboxylic acids.

* * * * *